United States Patent [19]
Eichinger

[11] Patent Number: 6,084,134
[45] Date of Patent: Jul. 4, 2000

[54] PROCESS FOR PREPARING 9-ANTHRACENECARBALDEHYES

[75] Inventor: Wolfram Eichinger, Köln, Germany

[73] Assignee: Bayer Aktiengesellschaft, Germany

[21] Appl. No.: 09/049,620

[22] Filed: Mar. 27, 1998

[30] Foreign Application Priority Data

Apr. 4, 1997 [DE] Germany .......................... 197 13 912

[51] Int. Cl.$^7$ ...................... C07C 47/52; C07D 215/227
[52] U.S. Cl. .......................... 568/439; 568/442; 568/437; 546/101; 546/79
[58] Field of Search .................................. 568/433, 437, 568/439, 442; 546/74, 101, 79, 110

[56] References Cited

FOREIGN PATENT DOCUMENTS 519 444   2/1927   Germany .

OTHER PUBLICATIONS

Archer et al, Journal of the American Chemical Society, vol. 75, pp. 989–991, 1953.

E. Campaigne et al., The Use of Dimethylformamide as a Formylation Reagent, *J. Amer. Chem. Soc.*, pp. 989–991, (1953). XP002072774.

F.H.C. Stewart, The Preparation of Some Surface Active Alcohols Containing the Anthracene Nucleus, *Aust. J. Chem.*, pp. 478–487, (1960). XP002072770.

L. Nedelec et al., La formyl–9 anthrone et ses formes tautomères énoliques: hyroxy–méthylène anthrone et hydroxy–9 anthraldéhyde–10, *Bull. Soc. Chim. Fr.*, pp. 1204–1216, (1960). XP002072771.

A. K. Singh et al., Bacteriorhodopsin Analog From Anthryl Chromophores, *Can. J. Chem.*, Bd 68, pp. 383–389, (1990). XP002072769.

P.K. Sen et al., Oxidation of 10–methoxy–9–anthraldehyde With Various Oxidising Agents in Protic and Aprotic Media, *Indian J. of Chem.* vol. 28B, pp. 978–979, (1989). XP002072772.

F. Effenberger et al., Synthesis of Conjugated Polyenes with Alkylanthryl and N–Alkylpyridinium Terminal Groups, *Synthesis*, pp. 1115–1120, (1995). XP002072773.

L.F. Fieser, et al., 9–Anthraldehyde; 2–Ethoxy–1–Naphthaldehyde, *Organic Syntheses Collective* vol. 3, pp. 98–100 (1955).

*Primary Examiner*—Shailendra Kumar
*Assistant Examiner*—Sreeni Padmanabhan
*Attorney, Agent, or Firm*—Brinks Hofer Gilson & Lione

[57] ABSTRACT

9-Anthracenecarbaldehydes are obtained in a particularly advantageous manner by reacting the corresponding anthracene derivatives with dimethylformamide in the presence of phosphoryl chloride, hydrolyzing the resulting reaction mixture and precipitating the 9-anthracenecarbaldehyde that is formed by admixing a base.

9 Claims, No Drawings

PROCESS FOR PREPARING 9-ANTHRACENECARBALDEHYES

BACKGROUND OF THE INVENTION

1. Field of the Invention

The present invention relates to a favorable process for preparing 9-anthracenecarbaldehydes. 9-Anthracenecarbaldehydes are useful intermediates for preparing crop protection agents and pharmaceutics.

2. Discussion of the Background

DRP 519 444 discloses a preparation of 9-anthracenecarbaldehyde where anthracene is reacted with N-methylformanilide in the presence of phosphoryl chloride (=phosphorus oxychloride=$POCl_3$) at 80° C., the reaction mixture is subsequently introduced into dilute hydrochloric acid, and the product, after short heating, is precipitated and recrystallized from glacial acetic acid. Later, this process was improved by employing 1,2-dichlorobenzene as solvent (Org. Synth. Coll. Vol. III, p. 98 (1958)), giving rise to yields of up to 84%. This procedure, however, has various disadvantages. Thus, N-methylaniline which is obtained as byproduct has to be disposed of in an ecologically safe way, or has to be re-used in the preparation of N-methylformanilide and recycled. N-methylaniline and, if appropriate, 1,2-dichloro-benzene have to be removed by steam distillation. Since 9-anthracenecarbaldehyde is also volatile in steam, some of the product is lost. Finally, the black oil that is initially obtained has to be recrystallized for purification in any case.

When dimethylformamide was used instead of N-methylformamide, a yield of 62.5% was obtained with 1,2-dichlorobenzene as solvent, and a yield of 45% was obtained when dimethylformamide was also used as solvent (J. Am. Chem. Soc. 75, 989 (1953)), but again, the recrystallization of the product could not be dispensed with. Preparation of 9-anthracenecarbaldehyde in almost quantitative yield is possible by reacting anthracene with a trifluoromethanesulfonic anhydride/dimethylformamide complex. In this process, however, the sodium trifluoromethanesulfonate that is obtained has to be recovered and recycled into the anhydride for economical and ecological reasons.

SUMMARY OF THE INVENTION

This invention, accordingly, provides a process for preparing 9-anthracenecarbaldehydes of the formula (I)

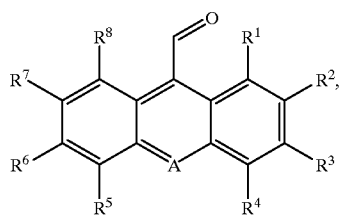

in which

A represents C—$R^9$ or N and $R^1$ to $R^9$ independently of one another each represent hydrogen, halogen, $C_1$–$C_6$-alkoxy, phenyl, naphthyl, anthracenyl, $C_1$–$C_4$-alkyl or $C_3$–$C_7$-cycloalkyl, which comprises reacting an anthracene derivative of the formula (II)

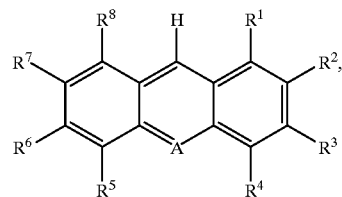

in which

A and $R^1$ to $R^9$ are each as defined in formula (I) with dimethylformamide in the presence of phosphoryl chloride, hydrolyzing the resulting reaction mixture and precipitating the 9-anthracenecarbaldehyde that has formed by admixing a base.

DESCRIPTION OF THE INVENTION

In the formulae (I) and (II), $R^1$ to $R^9$ independently of one another each preferably represent hydrogen, fluorine, chlorine, bromine, methoxy, ethoxy, methyl, ethyl, n-propyl, i-propyl, n-butyl or t-butyl.

Furthermore, up to 4 of the radicals $R^1$ to $R^9$ preferably represent one of the abovementioned substituents and the remaining radicals preferably represent hydrogen. Particularly preferably, up to 2 of the radicals $R^1$ to $R^9$ represent one of the abovementioned substituents, and the remaining radicals particularly preferably represent hydrogen. Very particularly preferably, unsubstituted anthracene is used.

The process according to the invention can be carried out, for example, at 50 to 150° C., preferably at 80 to 120° C. The process can be carried out at atmospheric pressure, elevated pressure or reduced pressure. It is preferably carried out at atmospheric pressure.

For example 1 to 5 mol, preferably 1 to 2.5 mol of phosphoryl chloride and 1 to 5 mol, preferably 1 to 2.5 mol of dimethylformamide are employed per mole of the anthracene derivative of the formula (I). For example 0.2 to 1.5 mol, preferably 0.5 to 1 mol of dimethylformamide are employed per mole of phosphoryl chloride.

The process according to the invention can be carried out, for example, by initially charging the anthracene derivative of the formula (I) and the phosphoryl chloride and metering in dimethylformamide at the desired reaction temperature, for example over a period of 0.5 to 48 hours. Preference is given to metering in times of 2 to 18 hours. The reaction partners may also be added in a different order.

It is advantageous to continue stirring the reaction mixture for some time in the temperature range from 50 to 150° C. after the addition of the last reactant has ended. The reaction mixture may be stirred, for example, for another 1 to 30 hours.

In the most simple case, the hydrolysis is carried out by introducing the reaction mixture into water. Hydrogen chloride evolves, and a dark red-brown solution is formed. The 9-anthracenecarbaldehyde that is formed is finally precpitated by adding a base. Suitable for this purpose are for example sodium hydroxide or aqueous sodium hydroxide solution.

It is favorable to adjust the temperature of the water which is used for carrying out the hydrolysis initially to, for example, 30 to 70° C., and to keep it at 35 to 90° C. during the hydrolysis. The addition of a base can be carried out for example in such a way that a pH of 0.5 to 7, preferably of 1 to 5.5, results. During the addition of the base, it is advantageous to keep the temperature in the range from 10 to 30° C., and to increase the temperature subsequently to 20 to 90° C., in particular to 30 to 80° C., and to stir the reaction mixture for some more time, for example for 0.5 to 5 hours, in this temperature range.

The 9-anthracenecarbaldehyde of the formula (I) that has been prepared is then present as a precipitate and can be isolated by mechanical separation, for example by filtration.

If the resulting 9-anthracenecarbaldehyde is to be purified further, it can, for example, be stirred with water, and the suspension that has formed is, for example, stirred for 0.5 to 5 hours at 20 to 80° C., filtered again and washed with water. In this manner, 9-anthracenecarbaldehydes can be obtained in yields of, for example, more than 97% and purities of more than 98%.

In comparison with the prior art, the process according to the invention affords 9-anthracenecarbladehydes of the formula (I) in a more simple and more economic way and in better yields and purities. The amounts of byproducts, wastewaters contaminated with organic materials, and salts (sodium chloride, phosphates, dimethylammonium salts) are reduced to a minimum, and tedious work-up steps, for example steam distillation, recrystallization, recycling of reactants and recovering solvents, are not required.

EXAMPLES

Example 1

520 g of phosphoryl chloride were initially charged in a vessel fitted with stirrer and reflux condenser, 300 g of anthracene were added, and 165 g of dimethylformamide were added dropwise with stirring at 85 to 90° C. over a period of 7 hours. The reaction mixture was subsequently stirred for another 19 hours at 85 to 90° C. After this time, the conversion was 99.8%. The resulting hot dark-red to black reaction mixture was introduced into a recipient vessel containing 2 l of water which had been heated to 50° C. and was stirred, and the temperature was kept at 50 to 60° C. during this operation. Violent evolution of hydrogen chloride gas occurred, and the gas was discharged via a reflux condenser. The resulting reaction mixture was cooled to room temperature. The pH was adjusted to 3.5 by adding solid sodium hydroxide (about 240 g) a little at a time, during which the temperature was kept at 30° C., and the mixture was then stirred at 60° C. for 1.5 hours. The 9-anthracenecarbaldehyde, together with a little unreacted anthracene, precipitated quantitatively. The precipitate was filtered off and freed from most of the mother liquor. The filter cake that remained was once again suspended in 2 l of water, stirred at 60° C. for 1.5 hours and filtered off, and the filter cake that was obtained was washed with 500 ml of water.

The solid was dried at 60° C., affording 340 g of 9-anthracenecarbaldehyde corresponding to a yield of 98%. The melting point of the product was 104° C., the 9-anthracenecarbaldehyde content was 99.7% (determined by GC) and the anthracene content was 0.3% (determined by GC). By elemental analysis, the following values were additionally determined:

Phosphorus content: <0.05%
Nitrogen content: <0.01%
Sodium content: <0.03%
Chlorine content: <0.05%.

I claim:
1. A process for preparing 9-anthracenecarbaldehydes of the formula (I)

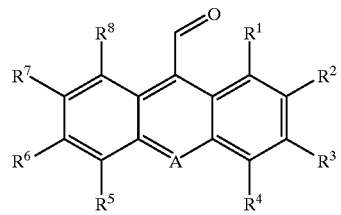

in which A represents C—$R^9$ or N, and $R^1$ to $R^9$ independently of one another each represent hydrogen, halogen, $C_1$–$C_6$-alkoxy, phenyl, naphthyl, anthracenyl, $C_1$–$C_4$-alkyl or $C_3$–$C_7$-cycloalkyl, which comprises (a) reacting an anthracene derivative of the formula (II)

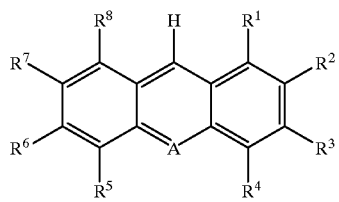

in which A and $R^1$ to $R^9$ are each as defined in formula (I), with a solvent consisting of dimethylformamide in the presence of phosphoryl chloride, (b) hydrolyzing the resulting reaction mixture, (c) precipitating the anthracenecarbaldehyde that has formed by admixing a base to form a first precipitate, (d) filtering the first precipitate, (e) stirring the filtrate with water for 0.5 to 5 hours at 20 to 80° C. to form a second precipitate, and (f) filtering the second precipitate;

wherein the process results in a yield of greater than 97% and a purity of greater than 98%.

2. The process as claimed in claim 1, wherein in the formulae (I) and (II) up to four of the radicals $R^1$ to $R^9$ represent one of the abovementioned substituents and the remaining radicals represent hydrogen.

3. The process as claimed in claim 1, wherein in the formulae (I) and (II) $R^1$ and $R^2$ independently of one another each represent hydrogen, fluorine, chlorine, bromine, methoxy, ethoxy, methyl, ethyl, n-propyl, i-propyl, n-butyl or t-butyl.

4. The process as claimed in claim 1, wherein the reaction is carried out at 50 to 150° C. and atmospheric pressure.

5. The process as claimed in claim 1, wherein 1 to 5 mol of phosphoryl chloride and 1 to 5 mol of dimethylformamide are employed per mole of the anthracene derivative of the formula (I) and 0.2 to 1.5 mol of dimethyl-formamide are employed per mole of phosphoryl chloride.

6. The process as claimed in claim 1, wherein the anthracene derivative of the formula (I) and the phosphorus oxychloride are initially charged and dimethyl-formamide is metered in over a period of 0.5 to 48 hours.

7. The process as claimed in claim 1, wherein the hydrolysis is carried out by introducing the reaction mixture into water, keeping the temperature in the range of 35 to 90° C.

8. The process as claimed in claim 1, wherein sodium hydroxide or aqueous sodium hydroxide solution is added as base at 10 to 30° C. in such a way that the pH after the addition is from 0.5 to 7.

9. The process as claimed in claim 1, wherein the reaction mixture is stirred for a further 0.5 to 5 hours at 20 to 90° C. after the addition of base has ended.

* * * * *